(12) United States Patent
Akutsu

(10) Patent No.: US 8,820,146 B2
(45) Date of Patent: Sep. 2, 2014

(54) CLEANLINESS INSPECTION APPARATUS AND CLEANLINESS INSPECTION METHOD FOR OBJECT TO BE INSPECTED

(75) Inventor: Shuichi Akutsu, Aiko-gun (JP)

(73) Assignee: NHK Spring Co., Ltd., Yokohama-shi, Kanagawa (JP)

( * ) Notice: Subject to any disclaimer, the term of this patent is extended or adjusted under 35 U.S.C. 154(b) by 443 days.

(21) Appl. No.: 13/178,123

(22) Filed: Jul. 7, 2011

(65) Prior Publication Data

US 2012/0024049 A1 Feb. 2, 2012

(30) Foreign Application Priority Data

Jul. 30, 2010 (JP) ................................. 2010-171900

(51) Int. Cl.
*G01N 15/06* (2006.01)
*G01N 29/032* (2006.01)
*B08B 3/12* (2006.01)
*B08B 3/00* (2006.01)
*G01N 15/02* (2006.01)

(52) U.S. Cl.
CPC ............... *G01N 29/032* (2013.01); *B08B 3/12* (2013.01); *G01N 15/0227* (2013.01); *B08B 3/00* (2013.01); *G01N 15/0625* (2013.01)
USPC ....................................................... 73/61.75

(58) Field of Classification Search
USPC .................. 134/184, 26, 36, 902; 377/11, 10; 73/61.75
See application file for complete search history.

(56) References Cited

U.S. PATENT DOCUMENTS

| | | | | |
|---|---|---|---|---|
| 3,102,737 A | * | 9/1963 | Williams et al. | ........... 280/414.1 |
| 3,631,714 A | * | 1/1972 | Cressman et al. | ............... 73/644 |
| 4,258,316 A | * | 3/1981 | Leif | .............................. 324/71.1 |
| 4,893,320 A | * | 1/1990 | Yanagi et al. | ................... 377/11 |
| 4,976,149 A | * | 12/1990 | Ichikawa et al. | ................ 73/597 |
| 5,090,430 A | * | 2/1992 | Nixon | ............................. 134/84 |
| 5,202,523 A | * | 4/1993 | Grossman et al. | ................ 42/95 |
| 5,339,842 A | * | 8/1994 | Bok | .................................. 134/1 |

(Continued)

FOREIGN PATENT DOCUMENTS

| | | |
|---|---|---|
| JP | 61-091388 U | 6/1986 |
| JP | 01-308942 A | 12/1989 |

(Continued)

OTHER PUBLICATIONS

Japanese Office Action dated Oct. 8, 2013 (and English translation thereof) in counterpart Japanese Application No. 2010-171900.

*Primary Examiner* — John Fitzgerald
(74) *Attorney, Agent, or Firm* — Holtz Holtz Goodman & Chick PC

(57) ABSTRACT

An ultrasonic generator tank includes an ultrasonic generator contains a first liquid in which ultrasonic waves propagate. A particle extraction vessel contains a high-purity second liquid, such as ultrapure water, and an object to be inspected. A power unit is turned on to oscillate the ultrasonic generator. The particle extraction vessel, which contains the second liquid and the to-be-inspected object, is inserted into the first liquid from above the surface thereof after the lapse of a first time since the start of oscillation of the ultrasonic generator. As the particle extraction vessel is inserted into the first liquid, the ultrasonic generator continues to produce ultrasonic waves. The quantity of particles contained in the second liquid is measured after the lapse of a second time.

7 Claims, 4 Drawing Sheets

(56) References Cited

U.S. PATENT DOCUMENTS

| | | | |
|---|---|---|---|
| 5,379,785 A * | 1/1995 | Ohmori et al. | 134/184 |
| 5,454,269 A * | 10/1995 | Vogt | 73/644 |
| 5,604,301 A * | 2/1997 | Mountford et al. | 73/54.31 |
| 6,016,821 A * | 1/2000 | Puskas | 134/186 |
| 6,026,832 A * | 2/2000 | Sato et al. | 134/184 |
| 6,352,469 B1 * | 3/2002 | Miyazaki et al. | 451/67 |
| 6,807,874 B2 * | 10/2004 | Totoki | 73/864.71 |
| 6,851,873 B2 * | 2/2005 | Muraoka et al. | 396/611 |
| 8,061,185 B2 * | 11/2011 | Monnoyer et al. | 73/61.42 |
| 2002/0026952 A1 * | 3/2002 | Fujino et al. | 134/1.3 |
| 2002/0079213 A1 * | 6/2002 | Demellayer | 204/238 |
| 2002/0185150 A1 * | 12/2002 | Namerikawa et al. | 134/1 |
| 2003/0041876 A1 * | 3/2003 | Tsuga et al. | 134/1.3 |
| 2003/0051552 A1 * | 3/2003 | Ilnicki et al. | 73/599 |
| 2003/0061881 A1 * | 4/2003 | Ibey | 73/597 |
| 2004/0074514 A1 * | 4/2004 | Sharma et al. | 134/1 |
| 2004/0182414 A1 * | 9/2004 | Puskas | 134/1 |
| 2005/0000301 A1 * | 1/2005 | Umekage et al. | 73/861.27 |
| 2005/0034742 A1 * | 2/2005 | Saito et al. | 134/1 |
| 2006/0037915 A1 * | 2/2006 | Strand et al. | 210/748 |
| 2006/0201532 A1 * | 9/2006 | Shirazi | 134/1 |
| 2007/0102020 A1 * | 5/2007 | Shiotsuki et al. | 134/1 |
| 2008/0295599 A1 * | 12/2008 | Clasen et al. | 73/599 |
| 2009/0044843 A1 * | 2/2009 | Shirazi | 134/115 R |
| 2010/0163083 A1 * | 7/2010 | Suzuki et al. | 134/184 |
| 2010/0192974 A1 * | 8/2010 | Matsumoto et al. | 134/1.3 |
| 2010/0294305 A1 * | 11/2010 | Abe et al. | 134/1 |
| 2010/0296976 A1 * | 11/2010 | Hakari et al. | 422/128 |
| 2011/0056512 A1 * | 3/2011 | Sato et al. | 134/1 |
| 2011/0079240 A1 * | 4/2011 | Kamikawa et al. | 134/1 |
| 2011/0139173 A1 * | 6/2011 | Akutsu | 134/1 |
| 2011/0278231 A1 * | 11/2011 | Nishijima | 210/695 |

FOREIGN PATENT DOCUMENTS

| | | |
|---|---|---|
| JP | 09-007992 A | 1/1997 |
| JP | 2000-354835 A | 12/2000 |
| JP | 2001-009395 A | 1/2001 |
| JP | 2001-035123 A | 2/2001 |
| JP | 2001-276760 A | 10/2001 |
| JP | 2006-247499 A | 9/2006 |
| JP | 2009-31173 A | 2/2009 |
| WO | WO 03102737 A2 * | 12/2003 |

* cited by examiner

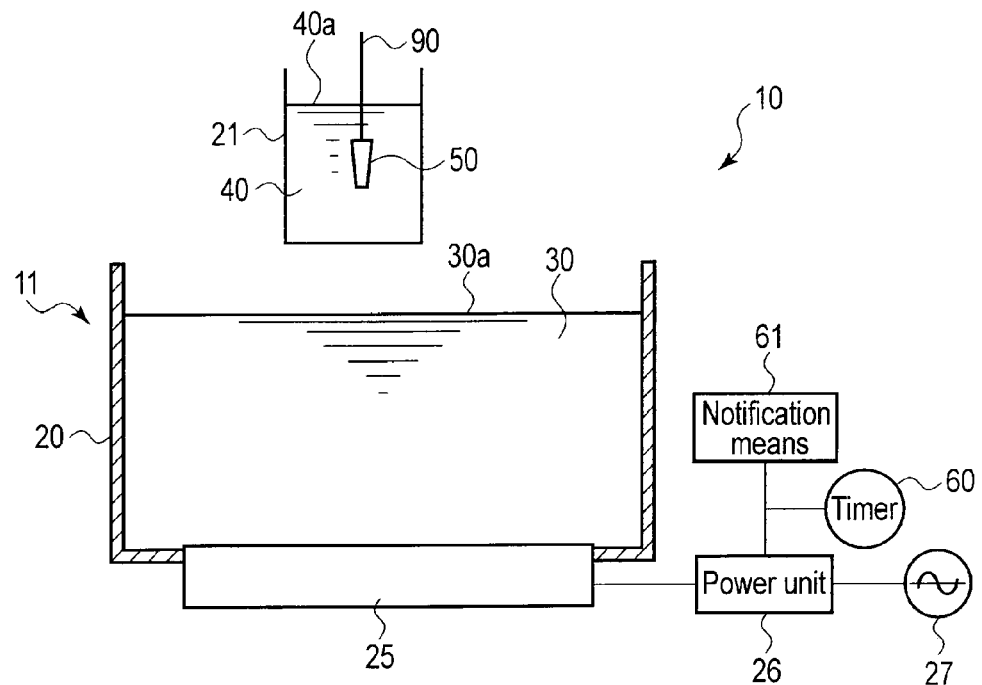
F I G. 1
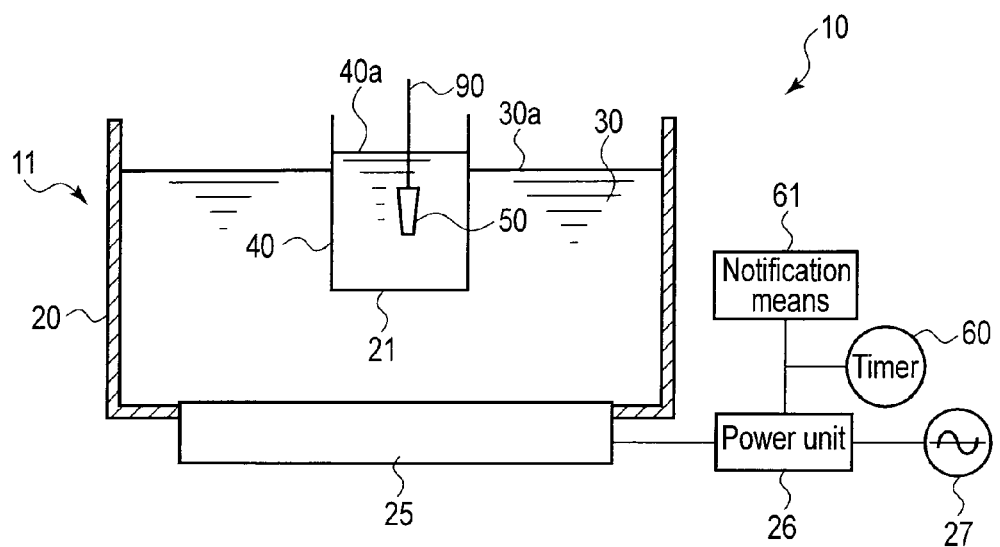
F I G. 2

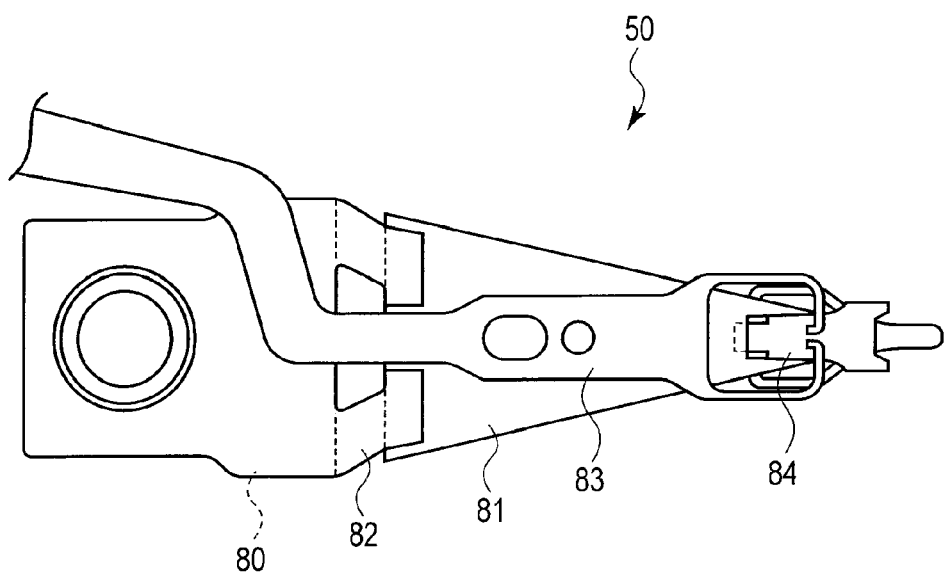
F I G. 5

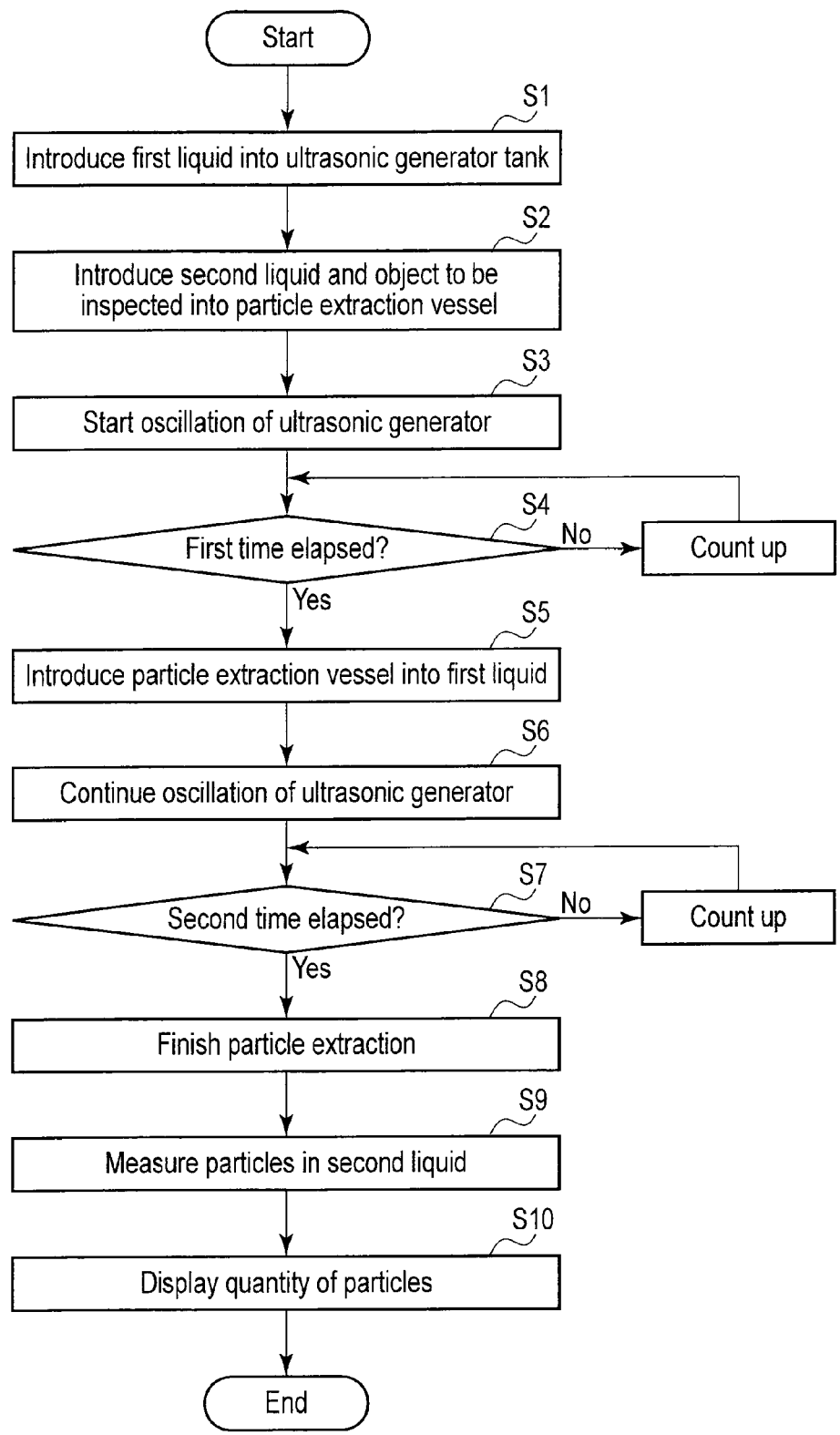
F I G. 6

CLEANLINESS INSPECTION APPARATUS AND CLEANLINESS INSPECTION METHOD FOR OBJECT TO BE INSPECTED

CROSS-REFERENCE TO RELATED APPLICATIONS

This application is based upon and claims the benefit of priority from prior Japanese Patent Application No. 2010-171900, filed Jul. 30, 2010, the entire contents of which are incorporated herein by reference.

BACKGROUND OF THE INVENTION

1. Field of the Invention

This invention relates to a cleanliness inspection apparatus and a cleanliness inspection method in which the cleanliness of an object to be inspected is detected by measuring the quantity of particles adhering to the to-be-inspected object.

2. Description of the Related Art

A hard disk drive (HDD) is used in a data processing apparatus, such as a personal computer. The hard disk drive comprises a magnetic disk rotatable about a spindle and a carriage turnable about a pivot, etc. A disk drive suspension is mounted on an arm of the carriage. The suspension comprises a load beam and a flexure superposed on it. A magnetic head comprising a slider is mounted near the distal end of the flexure. The magnetic head is provided with elements (transducers) for accessing data, that is, for reading or writing data. As the magnetic disk rotates at high speed, an air bearing is formed between the head and a surface of the disk.

The suspension is an ultra-small precision component, and the magnetic head is located close to or at a nanometer-order distance from the recording surface of the disk. If contaminants such as particles (solid granules) are sandwiched between the disk and head, therefore, the head or the recording surface of the disk may be damaged and rendered malfunctioning.

Since the suspension, disk, etc., are accommodated in a sealed case, particles can be prevented from being intruded into the disk drive. If particles adhere to the suspension itself at the stage of its production, however, they may sometimes separate from the suspension during use of the disk drive. In addition, the separated particles may get in between the disk and head. Since the suspension is located close to the recording surface of the disk, in particular, the particles separated from the suspension may cause a head crash in some cases. Therefore, it is important to maintain the cleanliness of the suspension at a high level.

A liquid particle counter (LPC) may be used to measure the cleanliness of a component such as the suspension that requires high cleanliness. For example, a component is inserted into a liquid in an ultrasonic generator tank in which an ultrasonic vibrator is accommodated, and ultrasonic vibration is applied to the component to separate particles from its surface. The number of particles contained in the liquid is counted by means of the particle counter.

An example of the liquid particle counter is described in Jpn. Pat. Appln. KOKAI Publication No. 2009-31173 (Patent Document 1). In this liquid particle counter, various liquids (media to be measured) to be used in semiconductor manufacturing processes are contained in a quartz glass cell. Ultrasonic vibration produced by an ultrasonic vibrator propagates in the liquids. Air bubbles in the liquids are removed by ultrasonic waves propagating in the liquids, and the numbers of particles in the liquids are counted.

An example of a supercritical extraction method is described in Jpn. Pat. Appln. KOKAI Publication No. 2006-247499 (Patent Document 2). According to this supercritical extraction method, a very small quantity of a sample to be extracted is inserted into a test tube, and in addition, methanol is introduced into the test tube to fill about half of its capacity. Then, the mouth of the test tube is closed. Thereafter, the test tube is inserted into a pressure-resistant stainless-steel vessel, and methanol is introduced into the vessel. Further, the pressure-resistant vessel is sealed and heated in an oven.

After ultrasonic waves are applied to objects to be inspected in a liquid, the quantity of particles can be inspected by means of the particle counter of Patent Document 1. In this inspection, however, the number of particles determined for each object may vary, although substantially equal quantities of particles adhere to the objects. One possible cause of this phenomenon is a substantial variation in particle extraction (or variation in the ratio of separation of particles adhering to the objects to be inspected).

Let us assume, for example, that the intensity of ultrasonic waves in an ultrasonic generator tank is measured by means of a sound-pressure meter. In this measurement, the ultrasonic intensity is not stable immediately after an ultrasonic generator is powered on, so that an excessive ultrasonic intensity may be produced immediately after the start of ultrasonic oscillation. If the ultrasonic generator is powered on with a to-be-inspected object in the generator tank, therefore, the instability of the ultrasonic intensity immediately after the start of oscillation causes variation in particle extraction. Immediately after the start of oscillation of ultrasonic vibration, moreover, the ultrasonic intensity cannot be easily stabilized because of the influence of dissolved gases and air bubbles in the liquid in the ultrasonic generator tank. This also causes variation in extraction.

Thereupon, a proposal has been made to insert an object to be inspected into the liquid after powering on the ultrasonic generator and waiting for a predetermined time to stabilize the ultrasonic intensity. Ultrasonic waves that propagate from the ultrasonic generator in the liquid toward the liquid surface are 100% reflected by the interface (liquid surface) between the liquid and air. The reflected ultrasonic waves are amplified at a depth equal to half the wavelength below the liquid surface such that an area with high vibrational energy is produced near the liquid surface. Thus, the quantity of extracted particles varies as the moving speed of the to-be-inspected object and ultrasonic vibrational energy vary when the object passes near the liquid surface.

Further, a very small object to be inspected, such as the suspension, may sometimes be caused to float on the liquid surface by surface tension as it is put into the liquid. In such a case, the time before the to-be-inspected object enters the liquid varies. Thus, the quantity of extracted particles varies according to each object to be inspected.

On the other hand, the supercritical extraction method described in Patent Document 2 requires specific processing, including a process for melt-sealing the mouth of a test tube containing a sample (object to be inspected), process for sealing the pressure-resistant vessel, etc. Thus, this method takes so much time that the cleanliness of objects to be inspected cannot be speedily inspected and entails high cost.

BRIEF SUMMARY OF THE INVENTION

The present invention provides a cleanliness inspection apparatus and a cleanliness inspection method for objects to be inspected, in which variation in particle extraction can be suppressed and appropriate inspections can be performed relatively easily.

A cleanliness inspection apparatus according to the invention comprises an ultrasonic generator tank, power unit, particle extraction vessel, and particle measuring device. The ultrasonic generator tank comprises an ultrasonic generator and contains a first liquid (e.g., tap water) in which ultrasonic waves propagate. The power unit supplies electric power for producing ultrasonic waves to the ultrasonic generator and continues to drive the ultrasonic generator until at least a second time elapses after the lapse of a first time since the start of oscillation of the ultrasonic generator. The particle extraction vessel contains a second liquid (e.g., ultrapure water) purer than the first liquid and accommodates an object to be inspected disposed in the second liquid. The particle extraction vessel is inserted into the first liquid from above the surface thereof after the lapse of the first time. The particle measuring device measures the quantity of particles contained in the second liquid after the lapse of the second time.

According to this arrangement, variation in particle extraction for each object to be inspected can be reduced, so that the cleanliness of the test object can be precisely determined based on the quantity of particles appropriately extracted from the to-be-inspected object.

The cleanliness inspection apparatus of the invention may further comprise means for measuring the first and second times and notification means configured to allow the particle extraction vessel to be inserted into the first liquid when the first time has elapsed and to notify expiration of particle extraction when the second time has elapsed. Further, the notification means may be configured to stop the ultrasonic generator when the second time has elapsed.

A cleanliness inspection method of the invention comprises introducing a first liquid into an ultrasonic generator tank comprising an ultrasonic generator, introducing a second liquid and an object to be inspected into a particle extraction vessel, supplying electric power for producing ultrasonic waves to the ultrasonic generator, introducing the particle extraction vessel, which contains the second liquid and the to-be-inspected object, into the first liquid from above the surface thereof after the lapse of a first time since the start of oscillation of the ultrasonic generator, causing the ultrasonic generator to continue to generate ultrasonic waves until at least a second time elapses after the lapse of the first time, and measuring the quantity of particles contained in the second liquid after the lapse of the second time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a side view schematically showing a particle extraction unit of a cleanliness inspection apparatus according to an embodiment of the invention;

FIG. 2 is a side view showing how a particle extraction vessel in the particle extraction unit of FIG. 1 is inserted into an ultrasonic generator tank;

FIG. 5 is a plan view showing an example of an object to be inspected; and

FIG. 6 is a flowchart sequentially showing steps of a cleanliness inspection method according to the embodiment of the invention.

DETAILED DESCRIPTION OF THE INVENTION

An apparatus and method for inspecting the cleanliness of an object to be inspected according to an embodiment of the present invention will now be described with reference to FIGS. 1 to 6.

Figure 3:
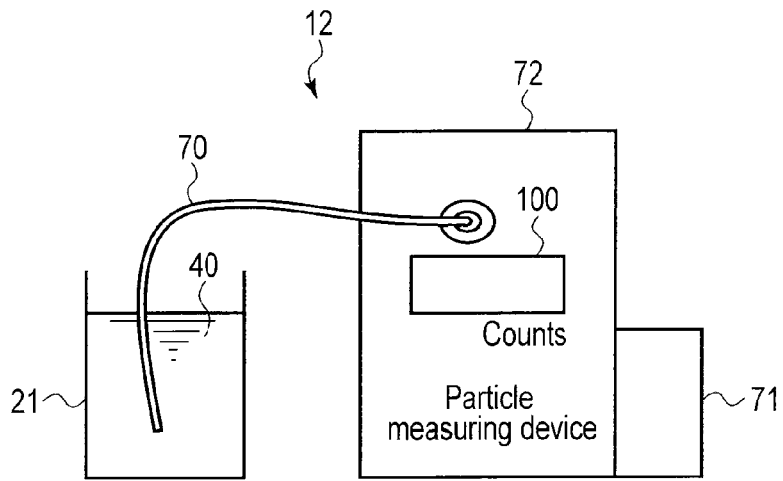
FIG. 3 is a side view schematically showing a particle detection unit.

A cleanliness inspection apparatus 10 comprises a particle extraction unit 11 shown in FIGS. 1 and 2 and a particle detection unit 12 shown in FIG. 3. The particle extraction unit 11 comprises an ultrasonic generator tank 20 and particle extraction vessel 21. An ultrasonic generator 25 is disposed at the bottom of the ultrasonic generator tank 20. The ultrasonic generator 25 is connected to a commercial power supply 27 through a power unit 26 comprising a driver circuit (pulsar).

The ultrasonic generator tank 20 contains a first liquid 30 in which ultrasonic waves can propagate. Tap water is a popular example of the first liquid 30 that is easily available at low cost. In short, the liquid 30 need only be a fluid in which ultrasonic waves can propagate, so that it may be of any kind. If the power unit 26 is turned on, the ultrasonic generator 25 is powered. Ultrasonic waves delivered from the ultrasonic generator 25 are directed to a surface 30a of the first liquid 30.

A glass beaker is an example of the particle extraction vessel 21. The vessel 21 contains a second liquid 40. Ultrapure water with containing minimal impurities, such as particles, is an example of the second liquid 40, which is purer than the first liquid 30. "High purity" implies the presence of a small quantity of impurity in the liquid.

The particle extraction vessel 21 accommodates a disk drive suspension as an example of an object (or sample) 50 to be inspected. The to-be-inspected object 50 is immersed in the second liquid 40. The object 50 may be a component other than the suspension.

The cleanliness inspection apparatus 10 comprises a timer 60 and notification means 61. The timer 60 serves as a means for measuring time having elapsed since the start of oscillation of the ultrasonic generator 25. The notification means 61 is activated when first and second times have elapsed since the start of oscillation of the ultrasonic generator 25. A display light is an example of the notification means 61. Alternatively, the notification means 61 may be an audio alarm, such as a beeper.

The notification means 61 is activated when a predetermined time (sum of first and second times T1 and T2) has elapsed after the activation of the power unit 26. When the notification means 61 is activated, an operator is informed of the lapse of the first and second times T1 and T2. The first time T1 is set to be longer than the time required for the stabilization of the ultrasonic intensity after the start of oscillation of the ultrasonic generator 25. For example, the first time T1 is set to about five to tens of seconds with a margin. The duration of this first time T1 is adjusted depending on the kind of first liquid 30 and other conditions. If tap water that is not degassed is used for the first liquid 30, for example, the first time T1 is set to be longer than in the case where degassed water with less dissolved gases is used for the purpose.

Figure 4:
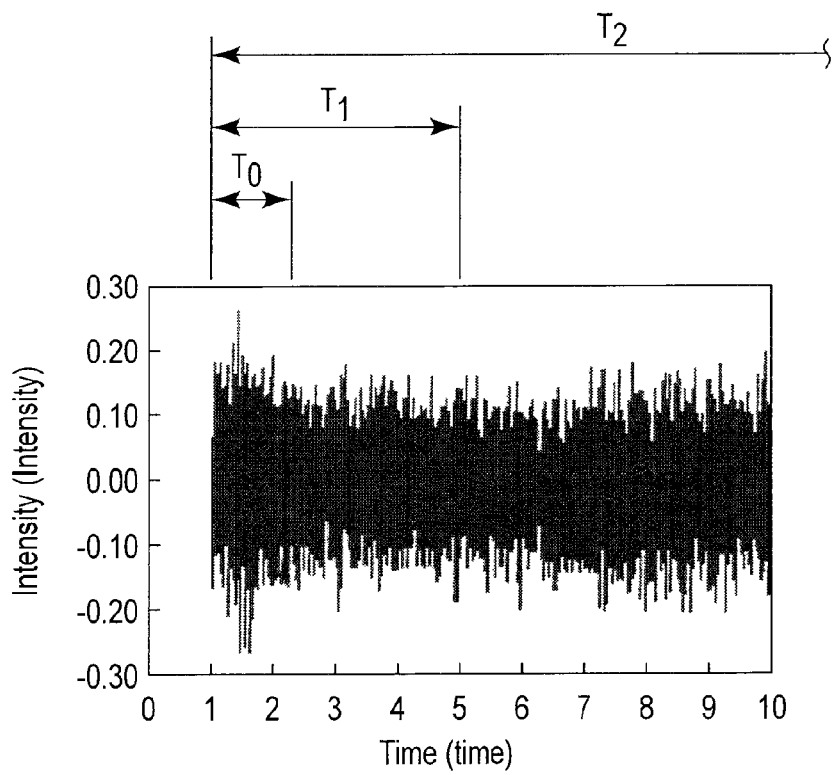
FIG. 4 is a diagram showing an example of time-dependent change of ultrasonic intensity measured in the ultrasonic generator tank.

FIG. 4 shows an example of results obtained by measuring the ultrasonic intensity after the start of oscillation of the ultrasonic generator 25 by means of a sound-pressure meter attached to the ultrasonic generator tank 20. In some cases, the ultrasonic intensity is unstable before the lapse of a time T0 immediately after the start of oscillation, and the peak of the ultrasonic intensity is observed. The first time T1 is set to be longer than the unstable time T0 during which the ultrasonic intensity immediately after the oscillation is unstable. When the notification means 61 notifies the lapse of the first time T1, the particle extraction vessel 21 is allowed to be inserted into the ultrasonic generator tank 20.

The second time T2 is a sufficient time to extract particles from the to-be-inspected object 50 by means of ultrasonic waves. The second time T2 is longer than the first time T1. The second time T2 is variably set depending on, for example, the kinds of the object 50 and liquids 30 and 40. When the notification means 61 notifies the lapse of the second time T2, the operator can notice the completion of the particle extraction from the object 50.

The particle detection unit 12 shown in FIG. 3 comprises a suction tube 70, pump 71, and particle measuring device 72. The suction tube 70 communicates with the second liquid 40 in the particle extraction vessel 21. The pump 71 draws in the second liquid 40. An example of the particle measuring device 72 comprises a plurality of types of filters having different apertures. Particles are trapped by these filters, and the number of particles trapped by each filter is counted for each particle size by means of a microscope. In this way, the size and number of particles contained in the second liquid 40 are detected.

A liquid particle counter using laser beams may be used as the particle measuring device 72. The liquid particle counter applies laser beams to a liquid containing particles and measures the intensity and number of scattered beams. The size of the particles in the liquid is determined by converting the intensity of the scattered beams to a particle size.

FIG. 5 shows the disk drive suspension as an example of the to-be-inspected object 50. The object 50 comprises a baseplate 80, load beam 81, hinge portion 82 formed of a thin plate spring, flexure 83, etc. Any of these components is formed of a metal such as stainless steel. The flexure 83 is disposed along the load beam 81. A gimbal portion 84 on which a magnetic head is to be mounted is formed near the distal end of the flexure 83.

A method for inspecting the cleanliness of the to-be-inspected object 50 by means of the cleanliness inspection apparatus 10 will now be described with reference to FIG. 6.

In Step S1 shown in FIG. 6, the first liquid 30 is introduced into the ultrasonic generator tank 20. In Step S2, the second liquid 40 and to-be-inspected object (sample) 50 are introduced into the particle extraction vessel 21. The object 50 is kept suspended below a surface 40a of the second liquid 40 by a suspension member 90 such as a strap (FIGS. 1 and 2). Alternatively, the second liquid 40 may be introduced into the particle extraction vessel 21 after the object 50 is inserted into the vessel 21. Further, Steps S1 and S2 may be simultaneously performed or Step S2 may be performed ahead of Step S1.

In Step S3, the power unit 26 of the ultrasonic generator 25 is turned on, whereupon the generator 25 starts to oscillate. Then, ultrasonic waves delivered from the generator 25 are propagated into the first liquid 30 and it is waited until the first time elapses.

If the lapse of the first time is detected by the timer 60 in Step S4, it is notified by the notification means 61. This notification allows the particle extraction vessel 21 to be inserted into the first liquid 30 in the ultrasonic generator tank 20. By this time, the second liquid 40 and to-be-inspected object 50 have already been introduced into the vessel 21 in Step S2.

In Step S5, the particle extraction vessel 21 containing the second liquid 40 and to-be-inspected object 50 is inserted into the first liquid 30 in the ultrasonic generator tank 20 from above the surface 30a of the liquid 30. When this is done, the first and second liquid surfaces 30a and 40a should preferably be visually aligned in position so that they are flush with each other. The ultrasonic generator 25 continues to generate ultrasonic waves (Step S6).

In Step S5, the to-be-inspected object 50 passes near the surface 30a of the first liquid 30 as the particle extraction vessel 21 is inserted into the first liquid 30. In the vicinity of the first liquid surface 30a, vibration is amplified at a depth equal to half the wavelength below the liquid surface 30a as the ultrasonic waves are 100% reflected by the interface between air and the first liquid 30. Therefore, a high-intensity area of vibration is produced near the liquid surface 30a. The object 50 is immersed in the second liquid 40 in the particle extraction vessel 21 as it passes near the liquid surface 30a. Thus, the object 50 can be prevented from being directly exposed to the high-intensity area of vibration near the liquid surface 30a. Consequently, variation in the quantity of extracted particles can be avoided.

In Step S5, the particle extraction vessel 21 is inserted into the first liquid 30 in the ultrasonic generator tank 20. While this state is maintained, ultrasonic waves continue to be generated from the ultrasonic generator 25 (Step S6). As the ultrasonic waves from the generator 25 propagate from the first liquid 30 to the second liquid 40, the to-be-inspected object 50 is subjected to ultrasonic vibration. Accordingly, particles separate from the object 50 and are extracted into the second liquid 40.

If the lapse of the second time is detected by the timer 60 in Step S7, it is notified by the notification means 61. By this notification, the operator can notice the completion of the particle extraction. The notification means 61 may have a function to stop the ultrasonic generator 25 (or the oscillation of ultrasonic waves) when the second time has elapsed.

In Step S8, the particle extraction vessel 21 is taken out of the first liquid 30 in the ultrasonic generator tank 20. In the particle detection unit 12 (FIG. 3), the number of particles in the second liquid 40 is counted by the particle measuring device 72 (Step S9). The counted number of particles is displayed on the display unit 100 of the particle measuring device 72 (Step S10). If the counted number of particles is not less than a predetermined value, the to-be-inspected object 50 is determined to be not sufficiently clean and be nonconforming. If the counted number of particles is less than the predetermined value, the object 50 is determined to be sufficiently clean and conforming.

As described above, the cleanliness inspection method of the present embodiment comprises the steps of:

(1) introducing the first liquid 30 into the ultrasonic generator tank 20;

(2) introducing the second liquid 40 into the particle extraction vessel 21;

(3) introducing the to-be-inspected object 50 into the particle extraction vessel 21;

(4) turning on the power unit 26 to oscillate the ultrasonic generator 25;

(5) introducing the particle extraction vessel 21, which contains the second liquid 40 and object 50, into the first liquid 30 in the ultrasonic generator tank 20 after the lapse of the first time, with the ultrasonic generator 25 continuing to generate ultrasonic waves;

(6) taking the particle extraction vessel 21 out of the ultrasonic generator tank 20 after the lapse of the second time;

(7) measuring particles in the second liquid 40 by means of the particle measuring device 72; and (8) displaying the determined quantity of particles.

According to the cleanliness inspection apparatus 10 and the cleanliness inspection method (Steps S1 to S10) described above, the particle extraction vessel 21 is inserted into the first liquid 30 with the first liquid 30 in the ultrasonic generator tank 20 sufficiently stabilized with regard to the ultrasonic intensity. The second liquid 40 and the to-be-inspected object 50 are previously contained in the particle extraction vessel 21. Thus, the ultrasonic intensity immediately after the start of oscillation of the ultrasonic generator 25 is not affected by an unstable time zone, so that one of the causes of the variation in the particle extraction can be removed.

In addition, the to-be-inspected object 50 can be previously sunk into the second liquid 40 in the particle extraction vessel 21 before the vessel 21 is inserted into the first liquid 30. The operation to sink the object 50 into the second liquid 40 is performed outside the ultrasonic generator tank 20. In this way, the object 50 can be prevented from being caused to float on the liquid surface 40$a$ by surface tension when ultrasonic waves are applied. Thus, the speed at which the object 50 passes through the liquid surface 40$a$ or the like can be prevented from causing variation in the particle extraction.

It is to be understood, in carrying out the present invention, that the configurations and layouts of the ultrasonic generator, particle measuring device, etc., and the states of the first and second liquids, as well as the shapes of the ultrasonic generator tank and particle extraction vessel, may be embodied in variously modified forms. Further, the object to be inspected may be any article other than a disk drive suspension that requires cleanliness control.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cleanliness inspection apparatus for an object to be inspected, the apparatus comprising:
    an ultrasonic generator tank comprising an ultrasonic generator and containing a first liquid in which ultrasonic waves propagate;
    a power unit which supplies electric power for producing ultrasonic waves to the ultrasonic generator, and which continues to drive the ultrasonic generator until at least a second time elapses after a lapse of a first time since a start of oscillation of the ultrasonic generator;
    a particle extraction vessel which contains a second liquid purer than the first liquid and accommodates the to-be-inspected object disposed in the second liquid, and which is adapted to be inserted into the first liquid from above a surface of the first liquid while the ultrasonic waves are being produced in the first liquid contained in the ultrasonic generator tank by the ultrasonic generator after the lapse of the first time; and
    a particle measuring device configured to measure a quantity of particles contained in the second liquid after the lapse of the second time.

2. The cleanliness inspection apparatus according to claim 1, further comprising:
    a timer which measures the first and second times, and
    notification means for initiating insertion of the particle extraction vessel into the first liquid when the first time has elapsed, and for notifying expiration of particle extraction when the second time has elapsed.

3. The cleanliness inspection apparatus according to claim 2, wherein the notification means is configured to stop the ultrasonic generator when the second time has elapsed.

4. A cleanliness inspection method for an object to be inspected, the method comprising:
    introducing a first liquid into an ultrasonic generator tank comprising an ultrasonic generator;
    introducing a second liquid and the to-be-inspected object into a particle extraction vessel;
    supplying electric power for producing ultrasonic waves to the ultrasonic generator;
    introducing the particle extraction vessel, which contains the second liquid and the to-be-inspected object, into the first liquid from above a surface of the first liquid while the ultrasonic waves are being produced in the first liquid contained in the ultrasonic generator tank by the ultrasonic generator after a lapse of a first time since a start of oscillation of the ultrasonic generator;
    causing the ultrasonic generator to continue to generate ultrasonic waves until at least a second time elapses after the lapse of the first time; and
    measuring a quantity of particles contained in the second liquid after the lapse of the second time.

5. The cleanliness inspection method according to claim 4, further comprising:
    stopping the ultrasonic generator when the second time has elapsed.

6. The cleanliness inspection method according to claim 4, further comprising:
    aligning respective surfaces of the first and second liquids when the particle extraction vessel is inserted into the first liquid.

7. The cleanliness inspection method according to claim 6, further comprising:
    stopping the ultrasonic generator when the second time has elapsed.

\* \* \* \* \*